United States Patent [19]

Brooks et al.

[11] Patent Number: 4,475,543
[45] Date of Patent: Oct. 9, 1984

[54] LUMBOSACRAL BRACE

[76] Inventors: William R. Brooks, 260 Arlington, Elmhurst, Ill. 60126; Irving C. Heinzel, 45 Brookdale La., Palatine, Ill. 60067

[21] Appl. No.: 458,467

[22] Filed: Jan. 17, 1983

[51] Int. Cl.³ .............................................. A61F 5/02
[52] U.S. Cl. .................................. 128/78; 128/89 R
[58] Field of Search ................... 128/78, 87 R, 89 R, 128/90, DIG. 20

[56] References Cited

U.S. PATENT DOCUMENTS

| 3,631,854 | 1/1972 | Fryer | 128/90 |
| 3,717,143 | 2/1973 | Johnson | 128/78 |
| 4,022,197 | 5/1977 | Castiglia | 128/78 X |

FOREIGN PATENT DOCUMENTS 1221134  5/1960  France ................... 128/DIG. 20

Primary Examiner—John D. Yasko
Attorney, Agent, or Firm—John S. Fosse

[57] ABSTRACT

An anatomic brace comprises a wide, elastic belt fashioned with a pouch, in combination with a semi-wrap-around polyurethane foam splint cured in place in the pouch while the belt is tightly fitted to the patient.

3 Claims, 6 Drawing Figures

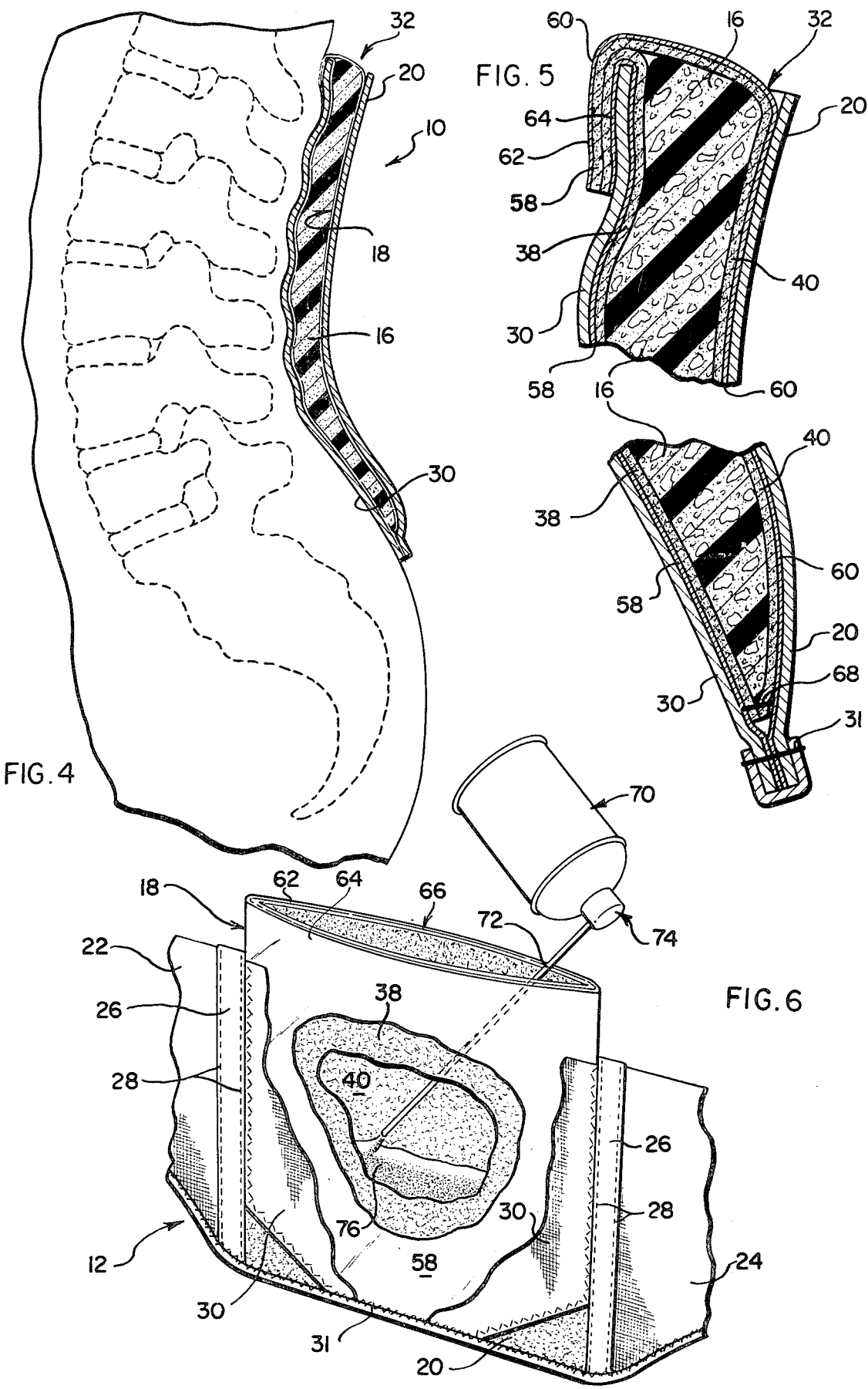

LUMBOSACRAL BRACE

FIELD OF THE INVENTION

This invention relates generally to orthopedic supports and braces and relates more particularly to an ambulatory brace for supporting the lumbosacral spine.

BACKGROUND OF THE INVENTION

Lower back pain has likely plagued mankind since the assumption of upright posture; and various diseases, malformations and injuries contribute to this problem. Subacute occurrences, however, have been acceptably managed in the past using an external support comprising various forms of splints and strapping. Nevertheless, lumbosacral braces have heretofore relied for strength and rigidity on such things as metal ribs and moldable thermoplastic splints and such methods of providing mechanical support do not afford truly intimate conformity with the patient's anatomy. The optimum efficacy of an external support has accordingly been compromised to the degree that the rigid bracing elements fail to conform exactly to the anatomical site and therefore permit undesired freedom of movement.

SUMMARY OF THE INVENTION

The present invention overcomes the limitations of the prior art by providing a wide, elastic belt with a pouch that is shaped to receive a comparatively fluid, incipiently curing polyurethane foam resin. While the foam resin is curing to a rigid state, the belt is strapped snugly on the patient; and the elasticity of the belt material acts to shape the resin into mating conformity with the confronting body region. The pouch and its contained foam splint are arranged to extend across nearly the entire posterior surface of the targeted patient's body region to provide semi-wrap-around support; and minimal manual manipulation of the moldable foam ensures a perfect fit. After the foamed resin has cured, the appliance may be worn in the usual fashion to afford anatomic support.

A general object of the present invention is therefore to provide a new and improved ambulatory anatomic brace.

A more specific object of the invention is to provide a lumbosacral support brace which automatically conforms itself, in its primary mode, to a broad region of the patient's anatomy.

Still another object of the invention is to provide an anatomic support which combines a washable belt with a removable and reinsertable splinting member.

Yet another object of the invention is to provide a comfortable, lightweight and highly effective anatomic brace.

These and other objects and features of the invention pertain to the materials and constructions by which the above objects are attained.

BRIEF DESCRIPTION OF THE DRAWINGS

In order that the principles of the invention may be readily understood, a single embodiment thereof, applied to a lumbosacral brace but to which the application is not to be restricted, is shown in the accompanying drawings wherein:

FIG. 4 is an enlarged, central cross-sectional view taken substantially along the line 4—4 of FIG. 1 to show the intimate mating conformity of the foam splint to the patient's anatomic contours;

FIG. 5 is a further enlarged cross-sectional view showing the mouth arrangement of the foam-receiving envelope folded over in its end-use condition; and FIG. 6 is a perspective view showing discharge of the fluid polyurethane composition into the envelope and its receiving pouch in the fabric belt, various layers of material being broken away to reveal details of construction.

DETAILED DESCRIPTION OF THE INVENTION

Figure 1:
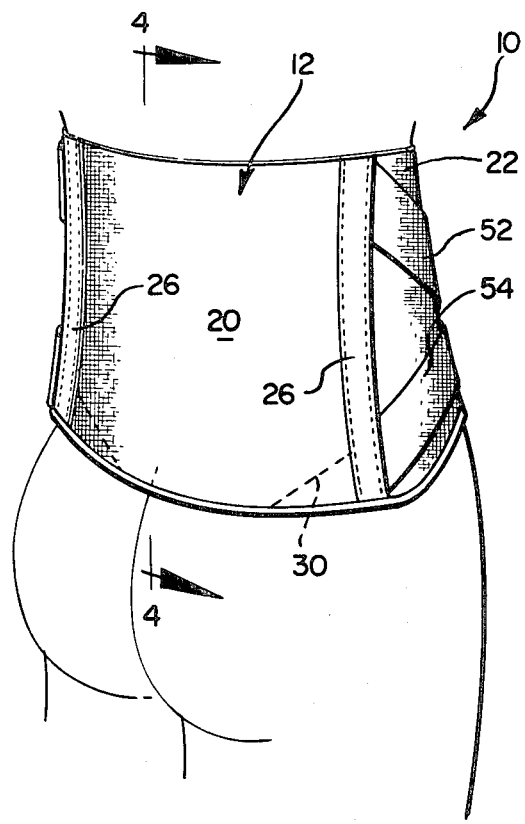
FIG. 1 is a right rear corner perspective view showing a lumbosacral brace constructed in compliance with the invention and secured in place on a patient.
Figure 2:
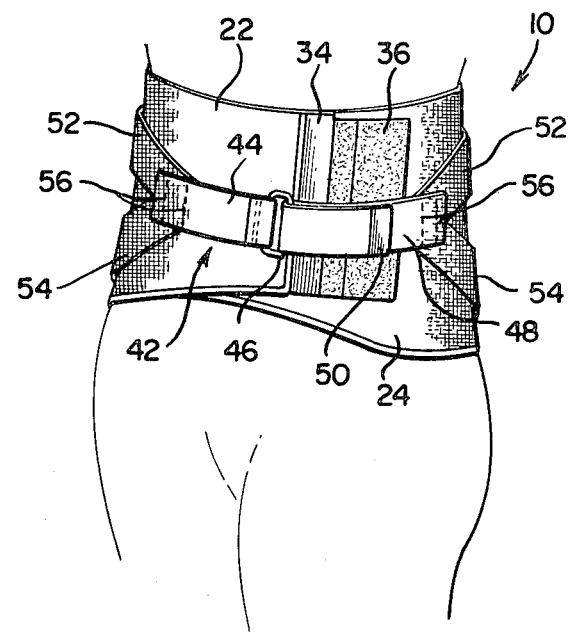
FIG. 2 is a front perspective view showing the lumbosacral brace of FIG. 1 in place on the patient.
Figure 3:
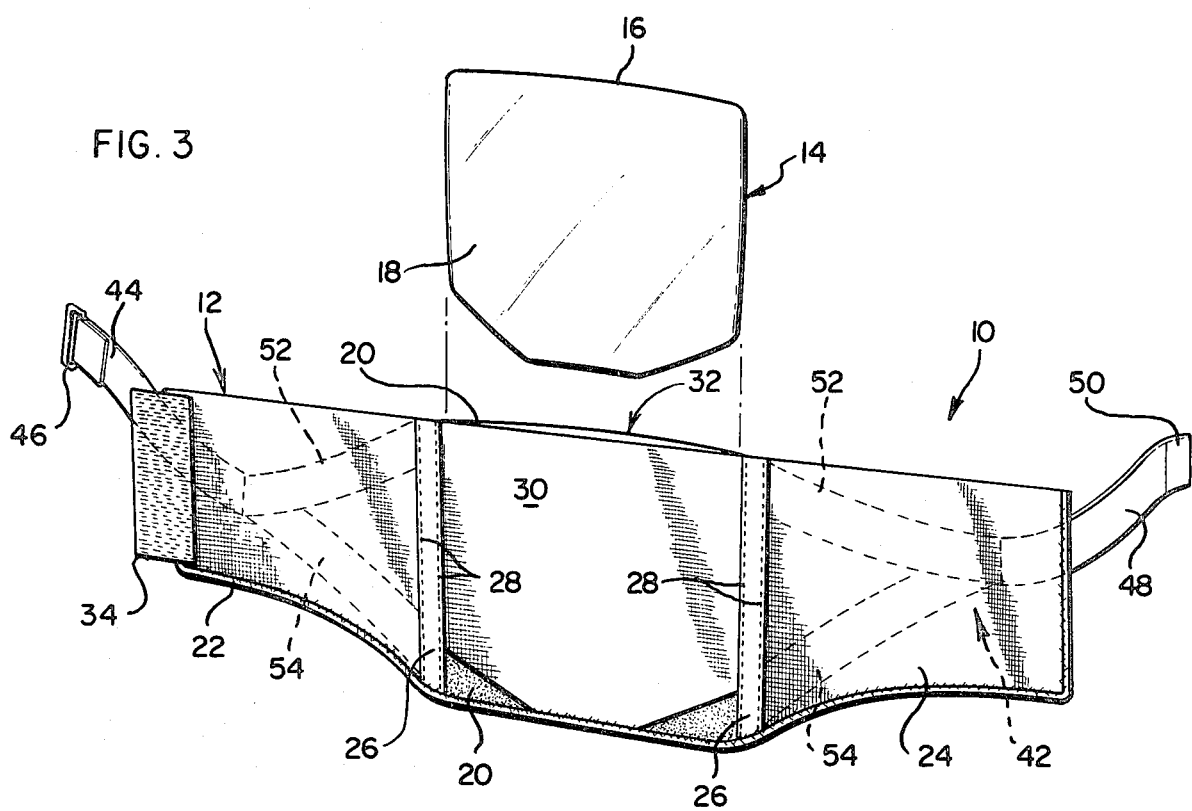
FIG. 3 is an inside, elevational view of the lumbosacral brace of FIGS. 1 and 2, shown with the polyurethane foam splint element and its enclosing envelope exploded away from the fabric belt arrangement.

Referring now to the drawings and giving first attention to FIG. 3 with secondary reference to FIGS. 1 and 2, an anatomic brace intended for ambulatory support of the lumbosacral region is indicated generally by the reference numeral 10. The anatomic brace 10 combines a fabric belt arrangement 12 and a support or splint member 14 which includes a rigid, lightweight polyurethane foam element 16 contained in a substantially impermeable, resinous plastic film envelope 18. According to the present invention, the foam element 16 extends across nearly the entire posterior, lumbosacral region in order to establish semi-wrap-around support.

The fabric belt arrangement 12 is fabricated with a central panel 20 which is adapted for placement generally confronting the patient's body region to be supported; and a pair of comparatively elastic side panels 22 and 24 are attached to respective side edges of the central panel 20 by suitable means such as vertical, reinforcing, aligned inner and outer fabric tapes or strips 26 and corresponding needle stitching 28. An inside, pocket panel 30 is secured to the central panel 20 by means including needle stitching 31 shown in FIG. 6, along its bottom edges, and by stitching 28 at its side edges, to define a splint-receiving, open-topped pouch 32 that is selectively sized to receive the rigid support member 14. In order to provide infinitely adjustable fastening means for interconnecting the free ends of side panels 22 and 24, whereby to close a snug-fitting loop encircling the patient's body, a strip 34 of "Velcro" fastening elements is sewn to the free end panel 22 and a strip 36 of cooperatively textured textile is sewn to the outside surface of the free end of panel 24, as is best seen in FIG. 2.

In order than the snug strapping of the fabric belt arrangement 12 around a patient's body region will act to store tensile forces, the purposes of which will be described more fully hereinafter, the side panels 22 and 24 are fabricated to be longitudinally elastic, as by selecting these panels to be of an elasticized textile such as "Spandex". In addition, the pocket panel 30 is similarly fabricated of elasticized fabric material in order that the pocket panel will respond resiliently to the molding action of the polyurethane foam element 16 while that element is in its fluid and unhardened state. The central panel 20 may comprise a comparatively inelastic fabric element although it, too, is preferably of an elasticized fabric in order to minimize wrinkling of the posterior outside surface of the anatomic brace.

The polyurethane foam composition for the element 16 is intended to be dispensed into the pouch 32 initially in a fluid, uncured, unhardened state; and in order to prevent adhesive attachment of the polyurethane resin to the fabric of panels 20 and 30, an open-topped envelope 18 of a suitable resinous plastic film material, such as polyethylene, is sewn into the pouch 32 by the lines of needle stitching 28 and 31. Furthermore and with reference to FIG. 6, the film envelope 18 is lined with confronting anterior and posterior panels 38 and 40 of a nappy, moisture-absorbent fabric. In forming the foam element 16 of splint member 14 in place on the patient, the panels 38 and 40, when suitably moistened, serve as a source or reservoir of the water that is necessary to the polymerization of the polyurethane resin, as will be described more fully hereinafter.

In order to provide supplemental tensioning forces and in order to facilitate repeated placement and removal of the anatomic brace 10, a system 42 of interengagable, comparatively inelastic straps is specially attached to the wide elastic belt 12. With reference to FIGS. 2 and 3, the strap system 42 comprises a first belt element 44 which has a plain buckle 46 affixed to its free end, and a second belt element 48 which has a strip 50 of "Velcro" fastener elements secured to its free end. In accordance with a feature of the invention, the belt elements 44 and 48 are specifically attached to the main belt 12 at the stitched vertical tapes 26 by respective convergent upper and lower straps 52 and 54. Thus disposed, the belt elements 44 and 48 can be used in drawing tensile forces into the panels 20 and 30. Conveniently, the straps 52 and 54 are connected to the belt elements 44 and 48 by lines of stitching 56, best seen in FIG. 2.

Turning to a consideration of FIGS. 5 and 6, the plastic film envelope 18 comprises inner and outer film panels 58 and 60 which extend beyond the upper edges of the panels 20 and 30 to provide a pair of envelope flaps 62 and 64 respectively, flaps 62 and 64 together defining an elongate open mouth 66. In addition and as is best seen in the lower portion of FIG. 5, the nappy fabric panels 38 and 40 are sewn to the bottom and sides of the plastic film panels 58 and 60 by means of respective stitching 68 which is spaced relatively inwardly from the lines of stitching 28 and 31. Thus, the stitching 28 and 31 establish lines of weakness at the boundaries of the bottom and sides of envelope 18; and because the fabric panels 38 and 40 are not incorporated in the patterns of stitching 28 and 31, the resultant lines of weakness define rupturable seams which permit the entire splint member 14 to be forceably separated from the belt arrangement 12 so that the fabric belt may be easily washed and dried and the splint member 14 conveniently reinserted for continued use of the brace 10.

In compliance with an important feature of the invention, the rigid foam element 16 of splint member 14 is formed in situ from a suitable polyurethane foam prepolymer composition; and with reference to FIG. 6, such a composition is packaged in a pressurized dispenser 70 which is assembled with an elongated discharge nozzle 72 and a suitable actuator valve arrangement 74.

When it is desired to fit the anatomic brace 10 to a patient, the pressurized dispenser 70 will first be readied, as by activating the contents with a suitable catalyst; and the resultant, fluid, incipiently reacting and foaming polyurethane composition 76 will be discharged from the dispenser 70 through the nozzle 72, which has been inserted through the open mouth 66 of envelope 18, and into contact with the premoistened nappy fabric panels 38 and 40, as is shown in FIG. 6. When a suitable quantity of the composition 76 has been dispensed into the film envelope 18, the flaps 62 and 64 will be folded over the pocket panel 30, as is suggested in FIG. 5, in order to contain the comparatively mobile resinous composition. Thereafter, the pouch 32 and its contents will be flattened and kneaded in order to physically work the foam composition, in order to suitably distribute it throughout the pouch, and in order to infuse portions of the resin into the interstices of the nappy fabric panels 38 and 40 in mechanically reinforcing relationship. Then, while the foam composition is still comparatively mobile, the brace 10 will be fitted to the patient with the pouch and its contents confronting the lumbosacral region, as is shown in FIG. 4. The belt arrangement 12 will be tightly stretched in order to develop tensile forces in the elastic elements of the belt arrangement; and the fastener strip 34 will be attached to the cooperatively textured strip 36 in order to retain this tension while the resinous composition flows into mating conformity with the anatomic site and subsequently cures in the resultant contoured condition. The auxiliary belt arrangement 42 will also be assembled and tightened to promote contouring of the foam composition; and manual manipulation of the foam in its mobile state will be employed to ensure a perfect fit.

Once the foam element 16 is cured and hardened, the anatomic brace 10 can be easily removed by unfastening the belt arrangement 42 and separating the strip of "Velcro" elements 34 from the textured surface of the textile strip 36. The brace 10 can thereafter be readily replaced in intimate mating conformity with the patient's lumbosacral region merely by retensioning the elastic belt elements and refastening them in place.

In order to enhance the understanding of the invention, it will be valuable, at this juncture, to described the dispenser 70 and its contents in greater detail. The dispenser 70 is selected to be a container or vessel of pressure-resistant construction and is factory-charged with a suitable quantity of a foamable, water-activatable polyurethane prepolymer composition. This composition comprises a prepolymer or polymer precursor, typically an hydroxyl-poor reaction product or adduct which is curable on contact with a source of water. This prepolymer is admixed with an inert polymer-miscible frothing or blowing agent. The resultant composition is packaged under such superatmospheric pressure that the blowing agent exists in substantially condensed or liquid form distributed throughout the prepolymer. In addition, this composition is capable of expanding, on release of the pressure and vaporization of the blowing agent, to form a foam which then cures rapidly on contact with moisture. In order to control the degree of initial frothing and in order to increase the ultimate strength of the cured foam, an insoluble, inert gas such as nitrogen may be used as a portion of the gas charge for dispensing the prepolymer composition from the containing vessel. Preferred compositions produce microcellular foams which ultimately contain at least about 40% and preferably between about 60% and about 70% open or reticulated cells.

A trimerizing catalyst is advantageously injected into and dispersed throughout the pressurized prepolymer mass immediately prior to dispensing the foam in making the anatomic brace 10. By thus increasing the reactivity of the foam composition at the moment of use, the present invention achieves a quick increase in the after-dispensed viscosity of the foam and also a fast "set time" in the resultant brace 16. Eminently useful, normally liquid, trimerizing catalysts are selected from such tertiary amines as N,N'N,"-tris-dialkylaminoalkyl-sym-hexahydrotriazine or N,N',N"-trialkyl-sym-hexahydrotriamine. The use of trimerizing catalysts in reacting isocyanates is described more fully in U.S. Pat. No. 2,993,870 to which reference is made for completeness of disclosure. A minimum of about 1½ parts of trimerizing catalyst per 100 parts of prepolymer by weight is required in the present invention, preferably from about 1.7 to about 3.0 parts per hundred. The selected tertiary amine catalyst may be used neat or mixed with a vehicle or with another catalyst such as dibutyltin dilaurate or a tertiary aliphatic amine.

The prepolymer used in the process of the invention may be any water-catalyzable liquid prepolymer or polymer precursor that, at ambient temmperature, has a sufficiently low viscosity to enable it to be dispensed at the desired rate but a sufficiently high viscosity, when catalyzed, to enable a stable foam or froth to be produced.

Polyurethane prepolymers are particularly suitable since they are water-catalyzable and hence may be cured by contact with the fabric panels 38 and 40 which have been moistened with a suitable quantity of water charged into the envelope 18. Polyurethane prepolymers have been fully described in the prior art and the factors influencing their viscosity are well known. In general, a polyurethane prepolymer is obtained by reacting an organic polyol with a controlled amount of an organic polyisocyanate, the product having unreacted isocyanate radicals which function to cure the resinous mass upon exposure to water and which trimerize in the presence of the described catalyst.

Polyurethane prepolymers for use in making an anatomic brace in accord with the invention may be prepared from any organic polyisocyanate that is liquid at ambient temperature and any organic polyol which has molecular weight of at least about 300 and which is also liquid at ambient temperature.

Several polyisocyanates have been described in the prior art for use in polyurethane processes, such as tolylene diisocyanate which is available as the 2,4-isomer or as mixtures of the 2,4- and 2,6-isomers. Any of the available grades may be used in distilled or crude form. Also useful are the crude diphenylmethane diisocyanate compositions, particularly those containing from 30% to 90%, preferably from 40% to 80%, by weight of diphenylmethane diisocyanate, the remainder being polyisocyanates of functionality greater than two.

Organic polyols suitable for use in making the polyurethane prepolymers of the invention include reaction products of one or more alkylene oxide compounds with a hydrogen-donor compound, such as ethylene glycol, propylene glycol, glycerol, sorbitol and various amino-alcohols. These reaction products desirably have molecular weights of between 300 and 8000 according to the amount of alkylene oxide reacted with the active hydrogen-containing compound. Other suitable polyols are polyesters which may be made, for example, from polycarboxylic acids and polyhydric alcohols.

The prepolymers of the invention are prepared by reacting the organic polyisocyanate with the organic polyol in known manner. The viscosity of the prepolymer will depend upon the constitution of the starting materials and on the amount of unreacted isocyanate. In general, the use of a polyol having a high functionality and a high hydroxyl number gives high viscosity prepolymers while the use of appreciable excesses of polyisocyanate tends to reduce the viscosity.

Prepolymers for use in the invention may conveniently be made by reacting an organic polyol with from 2 to 5 mol equivalents of an organic polyisocyanate. For a rigid foam, the use of approximately 3 to 4 mol equivalents of polyisocyanate per mol of polyol has been found to be preferable.

The frothing or blowing agent used in the present invention is material which is medically safe, which is inert towards the other ingredients of the system, and which has a sufficiently low boiling point to enable it to vaporize rapidly when the pressure on the system is released. Suitable inert blowing agents are those that have already been proposed for use in making polyurethane foams, including halogenated hydrocarbons having boiling points not exceeding about 50° C. at atmospheric pressure and particularly the fluorinated hydrocarbons. Dichlorodifluoromethane is an especially suitable blowing agent because of its low boiling point. In situations where it is desired to use lower pressures, a mixture of dichlorodifluoromethane and trichlorofluoromethane is more suitable because of the lower volatility of such a mixture. The amount of frothing or blowing agent in the formable compositions may be varied according to the foam density which it is desired to achieve and may range from 10% to 100% or more based on the weight of the prepolymer.

The foamable compositions prepared in accordance with the invention may also contain other conventional ingredients of polyurethane foam formulations, including suractants, such as organosilicon polymers, which serve to stabilize the foam until cure has taken place.

The foamable compositions of the present invention are converted into foamed plastics material by infusing with catalyst and releasing the pressure on the resinous mass by discharge to the ambient. On reducing the pressure, the foamable composition expands rapidly to give a froth, the final volume of which is quickly attained. Because initial foaming is entirely due to the release of pressure and not to vaporization caused by the heat resulting from a chemical reaction, the initial volume of the froth tends to remain substantially unchanged after equilibrium with ambient pressure has been achieved.

Upon contact with water, cure of the polymeric froth takes place beginning at the surface and then proceeding inwardly of the foam mass as a result of the diffusion of moisture into the foam; and comparatively rigid foam formulations are selected in order to provide proper mechanical support for the human body part. Such rigid foams are produced from polyols having from 3 to 8 hydroxyl groups per molecule and hydroxyl numbers of from 200 to 800, preferably 400 to 600.

The foamable compositions of the invention are prepared in bulk and then charged into containers of appropriate size, the pressure being releasable at the time of making the anatomic brace by a suitable valve arrangement. The containers may vary in size, or in the quantity of their contents, according to the volume of the support or brace that is to be made.

The drawings and the foregoing descriptions are not intended to represent the only forms of the invention in regard to the details of its construction and manner of operation. Changes in form and in the proportion of parts, as well as the substitution of equivalents, are contemplated as circumstances may suggest or render expedient; and although specific terms have been employed, they are intended in a generic and descriptive sense only and not for the purpose of limitation, the scope of the invention being delineated in the following claims.

The invention is claimed as follows:

1. The method of providing an anatomic support which comprises the steps of: fashioning an elastic fabric belt arrangement with a pocket closed on three sides and having an open, selectively closable mouth; charging a selected quantity of viscously fluid, flowable, permanently hardenable, polymeric brace material into said pouch; closing the mouth of said pouch; immediately stretching and snugly strapping said belt arrangement around a patient's body region to be supported, tensile forces generated in said belt arrangement, as a result of stretching it, acting to cause said brace material to flow, while in its unhardened state, into intimate conformity with the confronting, patient's body region; and allowing said brace material to harden in continuation of the application of said tensile forces whereby to form a permanently individually contoured splint shape.

2. The method according to claim 1 wherein said brace material is a water-reactable, polyurethane foam prepolymer and wherein water for curing said prepolymer is provided in said pouch.

3. An anatomic support made in accordance with the method of claim 1.

* * * * *